(12) United States Patent
Uihlein (10) Patent No.: US 9,895,159 B2
(45) Date of Patent: Feb. 20, 2018

(54) MULTIWIRE UNIT AND METHOD FOR PRODUCING THE SAME

(75) Inventor: Bernhard Uihlein, Dettingen (DE)

(73) Assignee: EPflex Feinwerktechnik GmbH, Dettingen/Ems (DE)

(*) Notice: Subject to any disclaimer, the term of this patent is extended or adjusted under 35 U.S.C. 154(b) by 1608 days.

(21) Appl. No.: 11/667,260

(22) PCT Filed: Nov. 5, 2005

(86) PCT No.: PCT/EP2005/011863
§ 371 (c)(1),
(2), (4) Date: Sep. 11, 2007

(87) PCT Pub. No.: WO2006/048314
PCT Pub. Date: May 11, 2006

(65) Prior Publication Data
US 2008/0311318 A1 Dec. 18, 2008

(30) Foreign Application Priority Data

Nov. 8, 2004 (DE) .................... 10 2004 055 375

(51) Int. Cl.
*B29D 22/00* (2006.01)
*A61B 17/221* (2006.01)

(52) U.S. Cl.
CPC .... *A61B 17/221* (2013.01); *A61B 2017/2212* (2013.01); *Y10T 428/13* (2015.01)

(58) Field of Classification Search
USPC ........ 294/100; 428/34.1; 140/71 R; 606/200, 606/113–114, 127–128, 151
See application file for complete search history.

(56) References Cited

U.S. PATENT DOCUMENTS 5,421,955 A * 6/1995 Lau et al. .................. 216/48
5,499,981 A   3/1996 Kordis
(Continued)

FOREIGN PATENT DOCUMENTS

DE  197 22 429 A1  12/1998
DE  101 17 836 C1   7/2002
(Continued)

OTHER PUBLICATIONS

International Search Report dated Jan. 23, 2006 with an English translation of the pertinent portions (Six (6) pages) and Form (PCT/ISA/237) dated Jan. 2004 (Five (5) pages).
(Continued)

*Primary Examiner* — Jennifer Chriss
*Assistant Examiner* — Ricardo Lopez
(74) *Attorney, Agent, or Firm* — Crowell & Moring LLP (57) ABSTRACT

A multiwire unit having a plurality of wire sections which are formed in one piece from a tubular piece whose tubular jacket is subdivided in at least an axial subsection by a plurality of axial slots. The wire pieces remain interlinked at a front end section at a distance to a front tube face, and assume a bent functional state downstream of the wire linking area in a defined functional state of the multiwire unit. The front wire linking area, in the functional state of the multiwire unit, is shaped to an essentially tipless front end closure. For this purpose, the axial slots end at an appropriate small axial distance to the front tube face. The multiwire unit may be formed as, for example, a wire basket unit or a wire filter unit for medical instruments.

9 Claims, 7 Drawing Sheets

(56) References Cited

U.S. PATENT DOCUMENTS

| | | |
|---|---|---|
| 6,013,086 A | 1/2000 | Ouchi et al. |
| 2002/0068954 A1 | 6/2002 | Foster |
| 2004/0026942 A1* | 2/2004 | Kessler et al. ............... 294/100 |
| 2004/0199243 A1* | 10/2004 | Yodfat ....................... 623/1.16 |
| 2005/0165442 A1* | 7/2005 | Thinnes et al. .............. 606/200 |

FOREIGN PATENT DOCUMENTS

| | | |
|---|---|---|
| WO | WO 98/36694 A1 | 8/1998 |
| WO | WO 01/87168 A1 | 11/2001 |

OTHER PUBLICATIONS

German Office Action dated Sep. 16, 2005 with English translation (Eight (8) pages).

* cited by examiner

MULTIWIRE UNIT AND METHOD FOR PRODUCING THE SAME

This application is a national stage of PCT International Application No. PCT/EP2005/011863, filed Nov. 5, 2005, which claims priority under 35 U.S.C. § 119 to German Patent Application No. 10 2004 055 375.0, filed Nov. 8, 2004, the disclosures of which are expressly incorporated by reference herein.

BACKGROUND AND SUMMARY OF THE INVENTION

The invention relates to a multiwire unit particularly for a medical instrument, and to a method of producing such a multiwire unit.

Multiwire units of this type are used, for example, as wire basket units, which may also be called wire cage or catching basket units, for medical instruments for catching and removing stones or other concretions from human or animal tissue canals. In the present context, the term "wire basket" means that several wire sections are arranged around a longitudinal axis of the wire basket unit at a distance from one another extending essentially axially in the circumferential direction. In a basket-forming condition, they extend from a forward end area of the wire basket unit, while forming the wire basket, first expanding radially toward the outside and then narrowing again radially toward the inside. The wire sections consist of a sufficiently elastic, not necessarily metallic material, frequently superelastic metal alloys being used.

Typically, the wire sections are guided in a rearward end area through a receiving sleeve into which they can be pulled while the wire basket shrinks radially. In the pulled-out basket-forming condition, a stone or the like can move into the widened wire basket through the spaces between the wire sections, after which, by a pulling of the wire sections into the receiving sleeve, the wire basket is drawn together and the stone can be retained for the removal.

Medical instruments of this type are used in various designs, for example, as endoscopes, such as stone catching basket instruments and balloon catheter instruments. For this and other applications, a forward end closure of the wire basket which is as short of possible is frequently desirable. In constructions, as disclosed, for example, in U.S. Patent Document U.S. Pat. No. 6,013,086, the forward wire section ends or forward end bows of wire loops are held in a cylindrical end sleeve which therefore remains disposed in front of the actual wire basket area.

German Published Patent Application DE 197 22 429 A1 discloses a device for catching and/or crushing objects in hollow organs, particularly gallstones or kidney stones, which is constructed as a multiwire unit of the above-mentioned type; that is, it contains several wire sections, which are formed in one piece from a tubular piece whose tubular jacket is subdivided in an axial partial area into the wire sections by several axial slots spaced in the circumferential direction. In this case, the wire sections remain mutually linked at a forward end area in that the axial slots end there while leaving a forward wire linkage area at a distance in front of a forward tube front end, and in a predefinable functional state of the multiwire unit following the wire linkage area, assume a bent small-basket forming functional state. In the case of this known multiwire unit, the axial slots end at a relatively large distance in front of the forward tube front end, so that a tip-forming forward end stub of the tubular piece remains which forms the wire linkage area. The distance of the axial slots from the forward tube front end is clearly greater than the diameter of the tubular piece and the width as well as the thickness of the wire sections. The tubular piece, which consists, for example, of nickel titanium wire and has the inserted wire sections, is used as a pull cord of this catching basket device. The axial slots are made, for example, by laser beam cutting. The forward tip end of the catching device may be equipped with a hemispherical end element and/or with a bordering ring visible by x-ray.

In contrast, so-called "tipless" wire basket units have been suggested. Thus, International Published Patent Application WO 98/36694 A1 describes wire basket units, where the basket-forming wire bows on the forward wire basket end, while forming narrower loops, are mutually linked loosely and thereby in an articulated manner. In German Patent Document DE 101 17 836 C1, it is suggested that the wire sections be held at the forward end in an articulated manner on a fixing body which may be designed such that, in the basket-forming condition, a virtually tipless forward end of the wire basket unit is obtained.

Furthermore, multiwire units are also used in medical instruments as wire filters, such as coronary filters, for catching deposits or clumping in tissue ducts, for example, for preventing emboli.

The invention is based on the technical problem of providing a multiwire unit of the initially mentioned type, which can be implemented in a tipless manner at comparatively low expenditures, and of providing a pertaining production method.

The multiwire unit according to the invention can be formed in one piece from a tubular piece in that several axial slots spaced in the circumferential direction are placed in its tubular jacket, which axial slots, while leaving a wire linkage area, end at a distance in front of a tube front end. As a result, the tubular jacket is divided into several wire sections which, in a section adjoining the wire linkage area, are bent to the shape desirable for a corresponding functional state of the multiwire unit, characteristically, the wire linkage area also deforming, so that an essentially tipless end closure is formed.

The invention therefore permits the production of a tipless multiwire unit made of only a single piece, that is, the tubular piece. The forward wire linkage area, by way of which the wire sections remain cohesively mutually connected at the forward end area, corresponding to the requirements, can be designed such that, when the wire sections are bent open or bent over correspondingly, for example, a virtually tipless wire basket or a virtually tipless wire filter with a desired maximal filtering width is obtained. For this purpose, the axial slots extend to a relatively narrow distance from the forward tube front end, so that, when the wire sections are bent open or over, the wire linkage area is also deformed and no noticeable axial tubular piece end stub remains; that is, in its functional state, the multiwire unit ends essentially in a tipless manner in that also the wire linkage area itself bends while the material is deformed.

As a person skilled in the art will understand, the term tipless indicates a forward end closure design of the multiwire unit which either has no axial end stub originating from the basic tubular piece or has only a very small end stub whose dimensioning and particularly whose axial length is negligibly small in comparison to the dimensions of the adjoining functional part formed by the wire sections, such as a wire basket or a wire filter; for example, only has an axial length which is by one or more orders of magnitude smaller than the maximal diameter of an adjoining wire basket. In particular, the term "tipless" or "essentially tipless" means that no remaining axial end stub projects abruptly toward the front from the adjoining functional unit formed by the wire sections, but the multiwire unit changes as early as from its forward end in a course bent open with respect to the tubular piece blank from the wire linkage area into the bent course of the wire sections in the functional unit.

In an advantageous embodiment of the invention, the tubular piece and thus the multiwire unit consists of a superelastic material. As a rule, such materials also have a shape memory. The latter can be utilized for selecting the functional state of the wire sections as the dimensionally stable state, so that the wire sections assume their functional state on their own when they are not prevented therefrom by outside forces, for example, by a sliding into a receiving sleeve, or are changed into a different state.

In a further development of the invention, the wire sections at the wire linkage area are bent by at least approximately 60°, as required by approximately 90° or more, relative to their axial tubular jacket position into the functional state. Thus, for example, a bending-open by approximately 90° permits the implementation of a completely bluntly ending wire basket which, at the forward end, with an at most slight axial component, expands essentially radially toward the outside, which is frequently desirable particularly for medical instruments, or of a wire filter which can also be used in medical instruments. For providing corresponding multiwire units, a bending-over of the wire sections by more than 90° may also be provided; that is, virtually, at least in areas, a turning-over of the tubular piece divided into the wire sections.

An embodiment of the invention provides an advantageous flexibility of the wire linkage area for forming the functional state of the multiwire unit in that the axial distance of the axial slots from the forward tube front end is selected to be smaller than an outside diameter and/or an inside diameter and/or to be approximately equally large as a or smaller than a wall thickness of the tubular piece and/or approximately equally large as or smaller than a width of the wire sections. Depending on the concrete other shaping of the wire linkage area, this permits a deforming of the end-side wire linkage area such that no noticeable axial end stub of the tubular piece remains; that is, a tipless end closure of the multiwire unit is achieved in a desired shaping of the wire linkage area.

In an advantageous embodiment of the invention, one or more slot-shaped recesses are placed in the tubular jacket from the front side of the tubular piece or adjacent thereto, which slot-shaped recesses are situated in the circumferential direction of the tubular piece at angular positions between the angular positions of the axial slots. By means of these slot-shaped recesses, the bending behavior of the wire sections in the wire linkage area and the shape of the wire linkage area in the functional state of the multiwire unit can be influenced in the respectively desired manner.

In an advantageous further development, the slot-shaped recesses extend axially into the area between the axial slots. In a further development, the axial slots are tapered in their area overlapping with the slot-shaped recesses; that is, they have a smaller width there than in their rearward portion outside this overlapping area. Advantageous shapes of the axial slots and of the slot-shaped recesses in the overlapping area are, for example, those with an essentially uniform width of the axial slots and of the slot-shaped recesses or those with axial slots oppositely tapering in a wedge-shaped manner and with slot-shaped recesses. Another advantageous shaping variant provides several rows of slot-shaped recesses following one another in the circumferential direction, these rows being offset in the axial direction and axially overlapping or not overlapping with one another.

In a further advantageous development of the invention, the tube front end is provided with an outer surrounding profiling, such as a wave-shaped profile. Also this measure can influence the shape of the wire linkage area in the functional state of the multiwire unit as well as the bending behavior of the wire sections in this area in a desired manner.

Objects, advantages and novel features of the present invention will become apparent from the following detailed description of the invention when considered in conjunction with the accompanying drawings.

DETAILED DESCRIPTION

Figure 1:
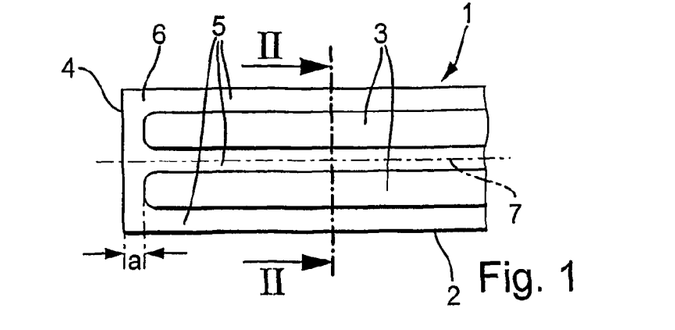
FIG. 1 is a lateral view of a forward area of a tubular piece with placed axial slots for producing a one-piece wire basket unit with four wire sections in accordance with an embodiment of the present invention.

FIG. 1 shows the forward part of a hollow tubular piece 1 that is of interest here and is used for the one-piece formation of a wire basket unit and consists, for example, of a superelastic material, particular one having a shape memory, such as an NiTi alloy, which is also known by the commercial name "Nitinol".

Figure 2:
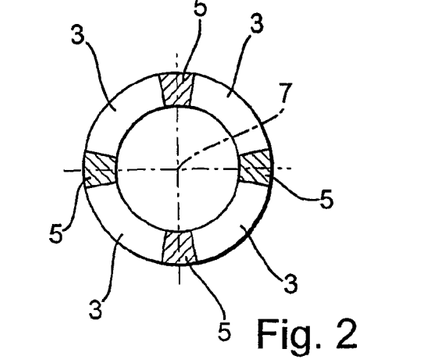
FIG. 2 is a cross-sectional view along Line II-II of FIG. 1.
Figure 3:
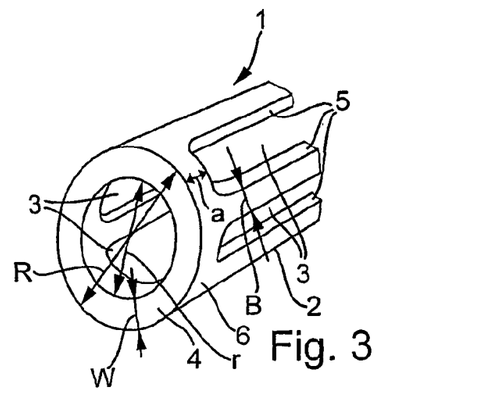
FIG. 3 is a perspective view of the front end area of the tubular piece of FIG. 1.

As illustrated in FIG. 1 in conjunction with FIGS. 2 and 3, four axial slots are placed in a tubular jacket 2 of the tubular piece 1, which axial slots 3 are spaced equidistantly from one another in the circumferential direction of the tube and, in the axial direction, end at a definable distance a in front of a pertaining tube front side 4. The four axially extending slots 3 divide the tubular jacket 2 into four wire sections 5 which are in each case mutually spaced by 90° in the circumferential direction of the tube. Since the axial slots 3 do not extend through to the tube front side 4 but end in front of the latter at the above-mentioned axial distance a, this forward tubular jacket section, which remains in an interconnected manner in the circumferential direction, forms a wire linkage area 6 by way of which the wire sections 5 are linked, that is, remain connected with one another.

Figure 4:
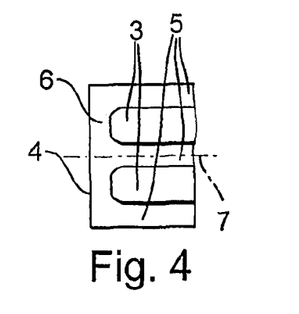
FIGS. 4 to 6 are lateral views of the forward end area of the tubular piece of FIG. 1 in a starting position, an intermediate position and an end position, respectively, during the bending-open of the wire sections generated by the axial slots from the tubular piece of FIG. 1 in a basket-forming condition.
Figure 5:
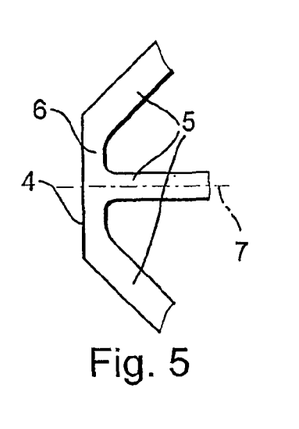
Figure 6:
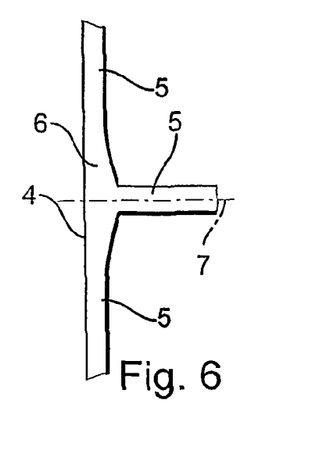
Figure 7:
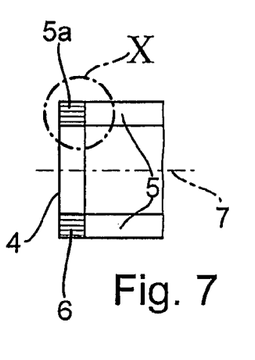
FIGS. 7 to 9 are longitudinal sectional views of the forward end area of the tubular piece of FIG. 1, which correspond to FIGS. 4 to 6.
Figure 8:
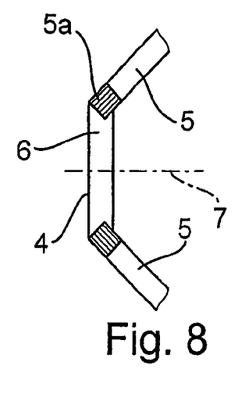
Figure 9:
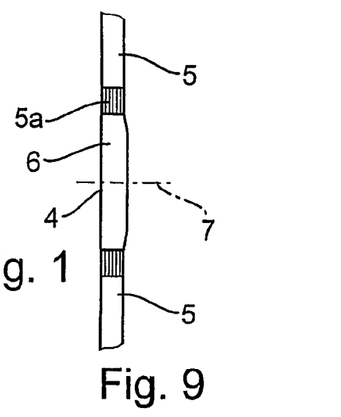
Figure 10:
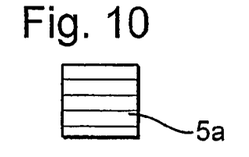
FIGS. 10 to 12 are views of details of a cutout-type area X of FIG. 7, which correspond to FIGS. 7 to 9.
Figure 11:
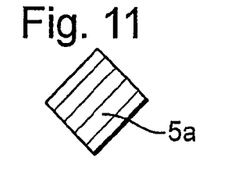
Figure 12:
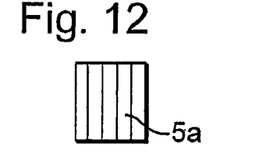

From the tubular piece 1 prepared in such a manner, a wire basket unit can be produced while the four wire sections 5 are deformed in a basked-forming fashion, as illustrated in FIGS. 4 to 14. For this purpose, the wire sections 5 are bent from their position parallel to the longitudinal axis 7 of the tubular piece and are deformed while forming a basket, in which case, they remain mutually connected in one piece in the distal forward wire linkage area 6 as well as in a not shown proximal rearward shaft area. In this case, a bending-open of the wire sections 5 by approximately 90° takes place in the wire linkage area 6. FIGS. 4 and 7 illustrate the forward tube end area before the bending operation; FIGS. 6 and 9 illustrate this tube end area after the bending over has been concluded; and FIGS. 5 and 8 illustrate an intermediate position after a bending-over by approximately half. FIGS. 10 to 12 show the bending process by means of an enlargement of the cutout X indicated in FIG. 7. In FIGS. 10 to 12, stripe-type lines symbolize the material orientation during the bending process in this area. This shows that, during the bending process, the wire sections 5 are bent over with their forward end area 5a by approximately 90° from their position parallel to the longitudinal axis 7 into a position perpendicular thereto pointing radially toward the outside, the wire linkage area 6 deforming correspondingly flexibly during the process.

Figure 13:
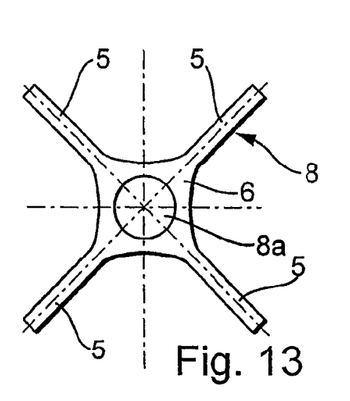
FIG. 13 is a top view of the forward side of the wire basket unit formed according to FIGS. 1 to 12.
Figure 14:
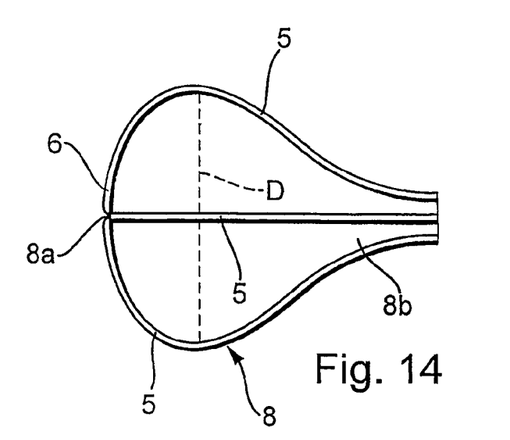
FIG. 14 is a lateral view of the wire basket unit of FIG. 13.

FIGS. 13 and 14 are a front view and a lateral view respectively of the wire basket unit generated by this bending process. As illustrated, in this basket-forming condition, the wire sections 5, while forming a wire basket 8 of the desired shape, are bent over such that a tipless basket forward end 8a is obtained which is formed by the wire linkage area 6. From the basket forward end 8a, the wire sections 5 first extend with a very small and then increasing axial component radially toward the outside before, starting from a maximal basket diameter D, they become radially narrower again and converge with the exception of a narrow radial space at the rearward basket end 8b.

This cobending or codeforming of the wire linkage area 6 during the bending of the wire sections 5 is permitted in that the axial slots 3 are appropriately placed in the tubular jacket 2 of the tubular piece 1, particularly at a sufficiently narrow distance a from the forward tube front side 4. As illustrated in FIG. 3, this axial distance a is particularly selected smaller than an outside diameter R and smaller than an inside diameter r of the tubular piece 1. Although not shown true to scale in FIG. 3, in advantageous embodiments, the axial distance a is many times smaller than the outside diameter R of the tube and is, for example, approximately in the order of magnitude of a wall thickness W of the tubular piece 1 and/or of a width B of the wire sections 5. Depending on the requirement and use, the axial distance a of the axial slots 3 from the forward tube front end 4 may also be smaller than the tube wall thickness W and/or the wire section width B.

In a conventional manner, which is not shown, the wire sections 5 may, for example, be axially displaceably held in a receiving sleeve. By pulling the elastic wire sections 5 into the receiving sleeve, the wire basket 8 can be increasingly narrowed. In this case, it can be provided that the wire sections 5 can be pushed completely into the receiving sleeve. When the wire sections 5 are moved out of the receiving sleeve, they resume their basket-forming condition.

By means of these functionalities, the wire basket unit can be used particularly as a medical catching basket instrument. For this purpose, while the wire sections 5 are pushed into the receiving sleeve, the wire basket unit is placed in a tissue duct, after which the wire sections 5 are pushed out of the receiving sleeve and form the expanded wire basket 8. Through the spaces between the wire sections 5, stones or other tissue deposits can be moved into the interior of the wire basket 8. The wire sections 5 are then withdrawn again, whereby the wire basket 8 narrows and holds the captured stores or deposits, so that they can then be transported out of the tissue duct.

The above description of the embodiment according to FIGS. 1 to 14 demonstrates that the invention permits the implementation of a wire basket unit at very low expenditures as a component produced in one piece from a tubular piece, particularly also in an embodiment with a tipless wire basket. The dimensioning of the wire basket unit, for example, with respect to the length and the cross-section of the wire sections, the diameter of the tubular piece, the thickness of the tubular jacket and the diameter of the wire basket, is therefore not subject to any specific limitations and can thus be freely based on the demands of the respective use. Thus, for example, for a use in medical catching basket instruments, tube diameters of between approximately 0.5 mm and approximately 2 mm are generally advantageous;

however, if required, any other diameters of the wire-basket-forming tube piece are also conceivable. The placing of axial slots 3 in the tubular jacket 2 can take place by an arbitrary method customary for this purpose, such as laser beam cutting or water jet cutting.

Additional advantageous implementations of wire basket units according to the invention are illustrated in FIGS. 15 to 28. For reasons of clarity, the same reference numbers are used in this case for identical or functionally equivalent elements.

Figure 15:
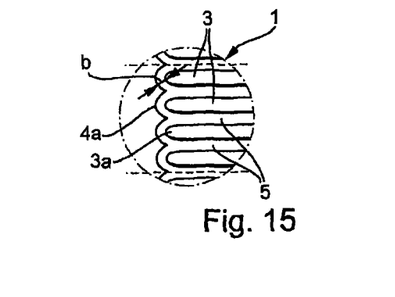
FIG. 15 is a developed view of the forward end area of a variant of the tubular piece of FIG. 1 with a tube front side profiled in a wave-shaped manner.
Figure 16:
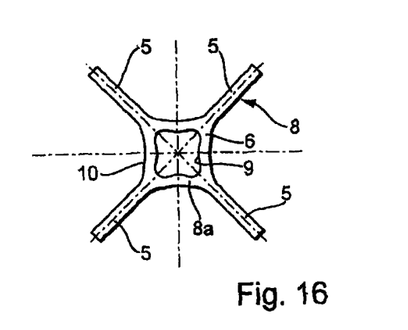
FIG. 16 is a top view of the forward side of the wire basket unit obtained from the tubular piece according to FIG. 15.
Figure 17:
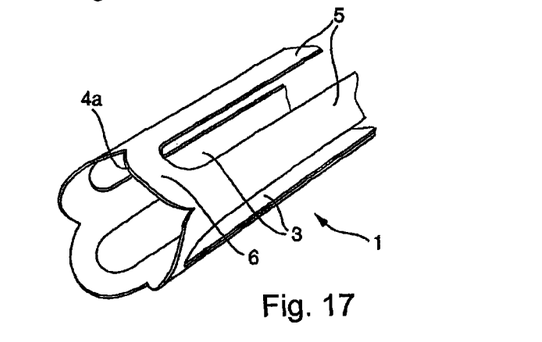
FIG. 17 is a perspective view of the forward end area of the tubular piece according to FIG. 15.

FIGS. 15 to 17 show a variant of the wire basket unit of FIG. 1 in which, instead of the linear tube front end 4 of the example of FIGS. 1 to 14, the tube front end of the tubular piece blank is provided with a wave-shaped outer profiling 4a, as illustrated in the developed view of the forward tube end area according to FIG. 15 and the perspective view of the forward tube end area according to FIG. 17. This wave-shaped profiling 4a corresponds with a correspondingly bluntly tapering forward closure 3a of the tube-jacket-dividing axial slots 3, so that, in this example, the wire linkage area 6 has an essentially constant axial width b and a wavy-line-shaped course over the entire tube circumference. FIG. 16 is a top view of the forward end of the wire basket unit obtained from this modified tube piece after the bending-open of the wire sections 5. In comparison to the embodiment of FIGS. 1 to 14—see particularly FIG. 13—, a modified course 9 of the interior edge is obtained which is not virtually circular as in FIG. 13, but rather follows the square outer edge course 10 of the wire linkage area 6.

Figure 18:
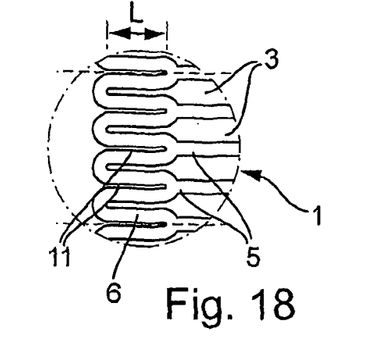
FIG. 18 is a developed view corresponding to FIG. 15 of a tubular piece variant having outwardly open, axially slot-shaped recesses between the and overlapping with the axial slots, the slot-shaped recesses and the axial slots in the overlapping area having a width which remains the same in each case.
Figure 19:
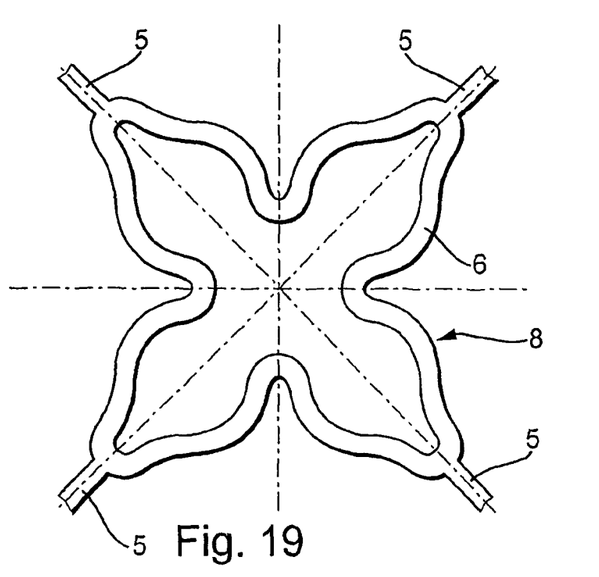
FIG. 19 is a top view corresponding to FIG. 16 of the forward side of the wire basket unit formed from the tubular piece of FIG. 18.
Figure 20:
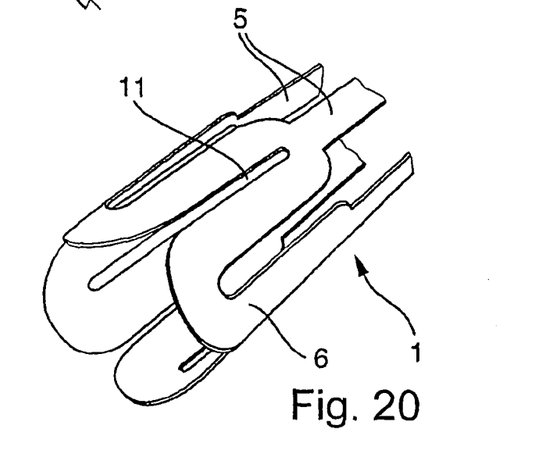
FIG. 20 is a perspective view corresponding to FIG. 17 of the wire basket unit of FIG. 19.

FIGS. 18 to 20 illustrate an example, in which slot-shaped axial recesses 11 stamped out from the forward front side of the tube are placed such in the circumferential direction alternating with the axial slots 5 ending at a distance in front of the front side of the tube that they overlap with the axial slots 5 over a certain axial length L. The axial slots 5 are tapered in the overlapping area L; that is, they have a smaller width in the overlapping area L than in the adjoining area behind it. In the overlapping area L, the axial slots 5 and the slot-shaped recesses 11 each have an essentially constant width. FIG. 19, in turn, is a top view of the forward end of the pertaining wire basket unit obtained after the bending-open of the wire sections 5. As a result of the slot-shaped recesses 11, in this example, the wire linkage area 6 is folded more and, if the wire basket parameters are otherwise the same, the wire linkage area 6 is more flexible for the bending-open of the wire sections 5 to the wire basket shape than in the case of the previously described embodiments.

Figure 21:
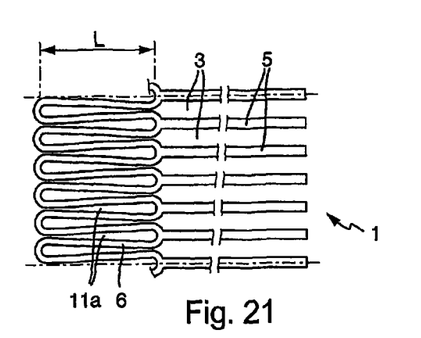
FIG. 21 is a developed view of the forward tube end area of a variant of the tubular piece of FIG. 18 with six wire sections and oppositely wedge-shaped slot-shaped recesses and axial slots.
Figure 22:
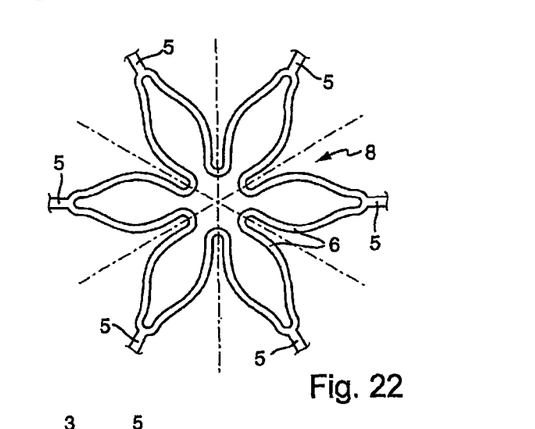
FIG. 22 is a top view corresponding to FIG. 19 of the forward side of the wire basket unit formed from the tubular piece of FIG. 21.

FIGS. 21 and 22 illustrate a variant in which the wire basket unit is formed of six wire sections 5 instead of four wire sections 5 from the previous embodiments, for which correspondingly six instead of four axial slots 3 are placed in the tubular piece blank 1, as illustrated in the tubular development of FIG. 21. Furthermore, in this embodiment, as in the embodiment of FIGS. 18 and 19, slot-shaped recesses 11a axially overlapping with the axial slots 5 are placed from the tube front side in an alternating manner with respect to the axial slots 5; that is, in the circumferential direction, with angular positions alternating with the angular positions of the axial slots 5. In contrast to the embodiment of FIGS. 18 to 20, the slot-shaped recesses 11a have a construction which is tapering in a wedge-shaped manner in the direction of the tube front end. Correspondingly, the axial slots 5 are shaped to be widening in a wedge-shaped manner in the direction of the tube front side. This construction of the slot-shaped recesses 11a and of the axial slots 5 in the overlapping area L leads to a further increased folding/bending capability of the wire linkage area 6. After the bending-open of the wire sections, a wire basket shape is then obtained whose forward end is visible in the top view of FIG. 22.

Figure 23:
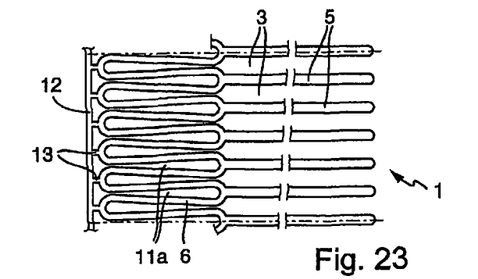
FIG. 23 is a developed view corresponding to FIG. 21 of a tubular piece variant with slot-shaped recesses closed toward the outside.

FIG. 23 is a view of a variant as a tubular development which largely corresponds to the embodiment of FIGS. 21 and 22, with the exception that the wedge-shaped axial slot recesses 11a are not placed such that they open to the tube front side but a narrow tubular jacket part 12 remains at the tube front end, by means of which tubular jacket part 12, the individual folds 13 of the wire linkage area 6 are mutually connected on the forward side.

Figure 24:
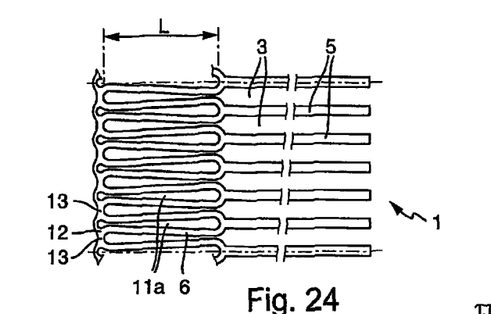
FIG. 24 is a developed view corresponding to FIG. 23 of another variant with slot-shaped recesses closed toward the outside.
Figure 25:
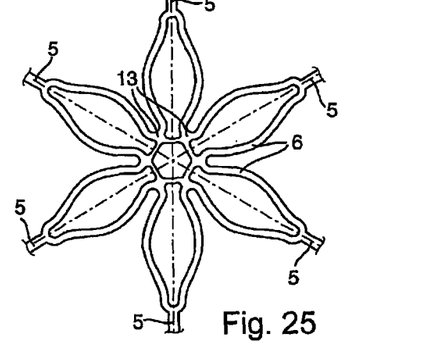
FIG. 25 is a top view corresponding to FIG. 22 of the forward side of the wire basket unit formed from the tubular piece of FIG. 24.

FIGS. 24 and 25 show an embodiment similar to the embodiment of FIG. 23, in which, differing from FIG. 23, a wave-shaped profiling of the tube front side is additionally provided. This has the result that the tubular jacket part 12 remaining in a surrounding manner on the tube front side correspondingly extends in the shape of a wavy line. FIG. 25, in turn, is a top view of the forward end of the wire basket unit obtained from the tubular piece 1 prefabricated in this manner after the bending-open and deforming of the wire sections 5.

Figure 26:
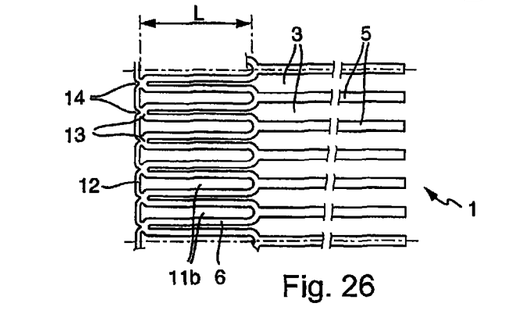
FIG. 26 is a developed view corresponding to FIG. 24 of a tubular piece variant having slot-shaped recesses of a constant width.
Figure 27:
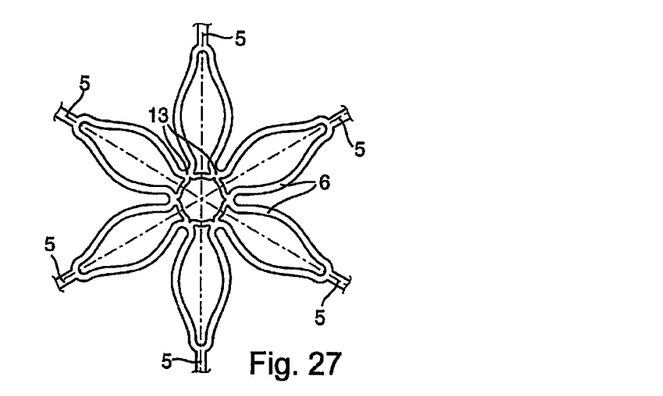
FIG. 27 is a top view corresponding to FIG. 25 of the forward side of the wire basket unit formed from the tubular piece of FIG. 26.

FIGS. 26 and 27 show a variant similar to FIG. 23, in which case, however, instead of the wedge-slot-shaped recesses 11a, slot-shaped recesses 11b of a constant width are provided. Furthermore, in this embodiment, the forward-side surrounding tubular jacket part 12 is profiled by being provided with slight notches 14 in the respective linkage area of a fold 13 of the wire linkage area 6. As a result, the forward end of the wire basket formed thereof has the appearance shown in FIG. 27.

Figure 28:
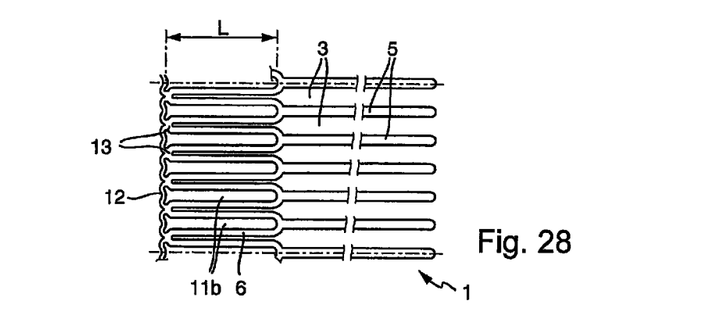
FIG. 28 is a developed view corresponding to FIG. 26 of another tubular piece variant with a modified shaping of the slot-shaped recesses.

In the tubular development, FIG. 28 shows a variant of the embodiment of FIGS. 26 and 27, in which the profiling of the surrounding tubular jacket part 12 remaining on the forward side is modified such that, instead of the linear course in the embodiment of FIGS. 26 and 27, the sections of this tubular jacket part 12 between the individual folds 13 of the wire linkage area extend in a wavy manner.

Figure 29:
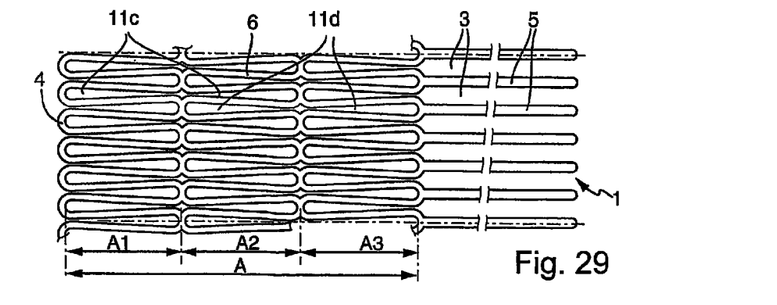
FIG. 29 is a developed view corresponding to FIG. 21 of a tubular piece variant having several rows of slot-shaped recesses.

In the tubular development, FIG. 29 shows a variant of the embodiment of FIG. 21, in which several axially offset rows of slot-shaped recesses 11a, 11c, 11d are provided within a forward axial tubular piece section A forming the wire linkage area 6. Especially in the illustrated example, in addition to the outer row of slot-shaped recesses 11a, which are open toward the tube front end 4 and are arranged successively in the circumferential direction, two additional rows of respectively closed slot-shaped recesses 11c, 11d are placed in this forward end area A of the tubular jacket, the closed slot-shaped recesses 11c, 11d in each of the two rows, like the slot-shaped recesses 11a open toward the tube front end 4, following one another in the circumferential direction at the same angular distance respectively. The slot-shaped recesses 11a, 11c, 11d are shaped in the manner illustrated in FIG. 29, with the effect that the remaining tubular jacket remains cohesively in one piece, and a corresponding shape for the wire linkage area 6 is obtained after the bending-open of the wire sections 5 by a desired bending-open angle.

As illustrated in FIG. 29, the closed slot-shaped recesses 11c, 11d of the two corresponding slot rows each have the shape of a double wedge consisting of two mirror-invertedly axially opposite wedge-shaped recesses, the two rows 11c, 11d overlapping in an axial area A2 with one wedge half respectively in an opposite wedge shape. By means of one half, the axially outer row 11c of closed slot-shaped recesses, in an outer axial area A1, overlaps with the open wedge-shaped recesses 11a in an opposite manner. By means of its axially inner double wedge halves, the inner row 11d of closed slot-shaped recesses, in an inner axial area, overlaps with the oppositely wedge-shaped ends of the wire-section-forming axial slots 3. The closed slot-shaped recesses 11$d$ of the inner row alternate in the circumferential direction with the axial slots 3. The closed slot-shaped recesses 11$c$ alternate in the circumferential direction with the closed slot-shaped recesses 11$d$ situated farther on the inside and are therefore situated at angular positions corresponding to the axial slots 3. The outwardly open slot-shaped recesses 11$a$ alternate in the circumferential direction with the axially overlapping with closed slot-shaped recesses 11$c$ and therefore correspond in their angular position with the axially interior closed slot-shaped recesses 11$d$.

On the whole, this perforation structure of the tubular jacket end area in the example of FIG. 29 results in a correspondingly complex but still one-piece wire linking area 6, as it is particularly advantageous for certain usages. Analogously, further variants according to the invention with arbitrary structures of slot-shaped recesses can be implemented which, if required, can also be placed with a noticeable circumferential direction component. For certain applications, at least some of the slot-shaped recesses can also be placed with a predominant circumferential direction component. As demonstrated by the above explanations, the term "axial slot" in this context relates only to those slot openings in the tubular jacket which are used for its division into the wire sections, while the term "slot-shaped recess" specifically indicates the openings in the forward end area of the tubular jacket forming the wire linkage area.

It is understood that, depending on the requirements, in addition to the illustrated wire basket units, further wire basket units can be implemented according to the invention, which can be produced in one piece from a tubular piece. The wire sections produced by dividing the tubular jacket can be bent into any arbitrary desired basket or balloon shape. In this case, it can be provided that the wire sections can be received in a receiving sleeve or the like and the basket diameter can thereby be variably adjusted. In addition to the illustrated examples with four or six wire sections, naturally also wire basket units with other arbitrary numbers of wire sections are conceivable in that the tubular jacket of the tubular piece blank is divided by the corresponding number of axial slots into the desired number of wire sections. In the same manner, the width, the length, the bending angle and/or the bending shape of the individual wire sections can be arbitrarily selected. If desired, different widths and/or different angular distances of the individual wire sections are also conceivable in this case. In addition, wire basket implementations are conceivable, where a bending-open of the wire sections at the wire linkage area by less than 90°, for example, only approximately 60°, or by more than 90°, for example, approximately 120°, is provided for achieving a corresponding wire basket shape. A turning over of the divided tubular piece is also conceivable, where the rearward wire section ends are bent over by approximately 180°, the forward wire section ends at the wire linkage area being bent open in a basket-forming manner, for example, by approximately 90° or any other bending angle.

In addition to the illustrated and above-described wire basket units, the invention comprises also other types of multiwire units, such as wire filter units, as they are also used in medical instruments. For forming such a wire filter, the wire sections, after the division of the tubular jacket, are bent open into the desired filtering function state, for example, by approximately 90°. The rearward wire section ends facing away from the wire linkage area then do not remain axially combined, as in the case of the wire basket formation, but remain fanned out in a desired length. As a result of the special shaping possibilities of the wire linkage area, as they are described above for the wire basket formation and also apply to the wire filter formation, when bending open the wire sections, the original tube opening can, as required, by appropriately narrowed such by deforming the wire linkage area that a desired maximal filter width is provided in order to be able to retain deposits, clumping, etc. which have comparatively larger dimensions. In this manner, for example, plane or funnel-shaped curved wire filter units can be implemented from a superelastic material. Depending on the usage, relatively small bending-open angles of clearly less than 90° may also already be sufficient for forming corresponding wire filters. However, as mentioned above with respect to the wire basket formation, a bending-over of the wire sections by more than 90° may also be provided in order to produce a wire filter unit of a corresponding shape. Furthermore, the structure of the slot-shaped recesses in the wire linkage area may be selected such that crossbar linkages of the tubular jacket remain, which extend essentially in the circumferential direction or in any case with a comparably smaller axial component and can contribute to achieving a desired filter netting structure with a relatively uniform mesh width.

While mainly the application possibilities for medical instruments were explained above, it is understood that the multiwire unit according to the invention is suitable for other arbitrary applications requiring a wire basket or wire cage, a wire filter or the like.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

The invention claimed is:

1. A multiwire basket unit, comprising:
a tubular piece having a tubular jacket divided at least in an axial partial area by a plurality of axial slots spaced in the circumferential direction to form a plurality of wire sections of the multiwire basket unit,
wherein
the axial slots extend to a predetermined distance from a forward end area of the tubular jacket,
the plurality of wire sections are mutually linked at the forward end area in a wire linkage area by a plurality of wire links at the distal ends of the axial slots,
the plurality of wire sections adjoining the wire linkage area assume a predefined bent functional state,
when in the bent functional state, the wire linkage area is deformed to an essentially tipless end closure, wherein edge faces of the plurality of wire links that are at least one of axially and circumferentially aligned when the plurality of wire sections are not in the bent functional state are aligned radially when the plurality of wire sections are in the bent functional state, and when in the bent functional state the plurality of wire sections first extend radially outward from the wire linkage area before extending axially away from the wire linkage area,
at least one slot-shaped recess is located in the tubular jacket and extends axially between adjacent axial slots,
said at least one slot-shaped recess being closed at an end opposite from the forward tube front area, and
said at least one slot-shaped recess being open in a direction toward the forward tube front end.

2. The multiwire unit according to claim 1, wherein the multiwire unit is formed of a superelastic material.

3. The multiwire unit according to claim 1, wherein the plurality of wire sections at the wire linkage area in the bent functional state are bent by at least approximately 60° with respect to a longitudinal axis of the tubular piece, and the axial distance of the axial slots from the forward tube front end is at least one of smaller than an outside diameter of the tubular piece, smaller than an inside diameter of the tubular piece, is essentially equal to or smaller than a wall thickness of the tubular piece, and essentially equal to or smaller than a width of one of the plurality of wire sections.

4. The multiwire unit according to claim 1, wherein the plurality of axial slots are tapered in an area axially overlapping with the at least one slot-shaped recess.

5. The multiwire unit according to claim 1, wherein in the overlapping axial area, the plurality of axial slots and the at least one slot-shaped recess are at least one of essentially uniform in width and tapering in an oppositely wedge-shaped manner.

6. The multiwire unit according to claim 3, wherein a plurality of axially offset circumferential rows of slot-shaped recesses are located at the forward end area of the tubular jacket, and the plurality of axially offset rows are mutually circumferentially offset and overlapping.

7. The multiwire unit according to claim 1, wherein the tube front end is provided with an outer profiling.

8. The multiwire unit according to claim 1, wherein the tube front end is provided with an outer profiling.

9. The multiwire unit according to claim 1, wherein the bent functional state is a wire basket unit.

* * * * *